(12) United States Patent
Tang et al.

(10) Patent No.: US 9,193,696 B2
(45) Date of Patent: Nov. 24, 2015

(54) CARBOXYLIC ACID TYPE WATER-SOLUBLE SULFUR DYE

(71) Applicant: DALIAN UNIVERSITY OF TECHNOLOGY, Dalian, Liaoning (CN)

(72) Inventors: Bingtao Tang, Liaoning (CN); Shufen Zhang, Liaoning (CN); Wei Ma, Liaoning (CN)

(73) Assignee: Dalian University of Technology, Dalian, Liaoning (CN)

(*) Notice: Subject to any disclaimer, the term of this patent is extended or adjusted under 35 U.S.C. 154(b) by 0 days.

(21) Appl. No.: 14/368,092

(22) PCT Filed: Nov. 30, 2012

(86) PCT No.: PCT/CN2012/085617
§ 371 (c)(1),
(2) Date: Oct. 9, 2014

(87) PCT Pub. No.: WO2013/091474
PCT Pub. Date: Jun. 27, 2013

(65) Prior Publication Data
US 2015/0065707 A1    Mar. 5, 2015

(30) Foreign Application Priority Data

Dec. 23, 2011 (CN) .......................... 2011 1 0438907

(51) Int. Cl.
*C07D 251/50* (2006.01)
*C07D 251/44* (2006.01)
*C07D 251/38* (2006.01)
*C09B 49/00* (2006.01)
*D06P 1/30* (2006.01)

(52) U.S. Cl.
CPC ............. *C07D 251/50* (2013.01); *C07D 251/38* (2013.01); *C07D 251/44* (2013.01); *C09B 49/00* (2013.01); *D06P 1/30* (2013.01)

(58) Field of Classification Search
CPC .... C09B 49/00; C07D 251/50; C07D 251/44; C07D 251/38
USPC ............................................ 544/215, 216, 14
See application file for complete search history.

(56) References Cited

U.S. PATENT DOCUMENTS

| | | | | |
|---|---|---|---|---|
| 4,284,770 A | * | 8/1981 | Tzikas | 544/187 |
| 7,476,260 B2 | * | 1/2009 | Eliu et al. | 8/405 |
| 7,488,354 B2 | * | 2/2009 | Daubress et al. | 8/405 |

* cited by examiner

*Primary Examiner* — Venkataraman Balasubramanian
(74) *Attorney, Agent, or Firm* — Zhi Yang Xue; Novick, Kim & Lee, PLLC

(57) ABSTRACT

The present invention provides a group of water-soluble sulfur dye having carboxyl groups. For the kind of dye, a sulfur dye is first reduced to a leuco compound by sodium sulfide, and the leuco compound reacts with an active compound containing carboxyl groups to obtain a water-soluble sulfur dye containing the carboxyl group. The water-soluble sulfur dye provided by the present invention is applicable to dying of cotton, wool, silk, and leather. Being both water-soluble and carboxyl group reactive, the product has a simple application process and desirable color fastness, thereby having broad application prospects.

6 Claims, 1 Drawing Sheet

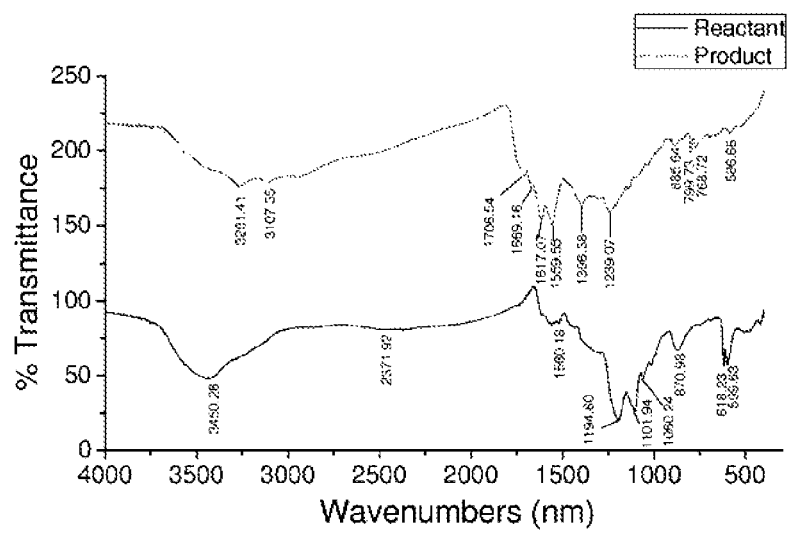

CARBOXYLIC ACID TYPE WATER-SOLUBLE SULFUR DYE

FIELD OF THE INVENTION

The present invention relates to a group of carboxylic acid type water-soluble sulfur dye.

BACKGROUND OF THE INVENTION

Sulfur dye is a group of dye containing sulfur. It contains sulfur bonds consisting of two or more sulfur atoms in its molecule. When in application, it can be reduced to leuco dye to dissolve in water and dye the fiber. The features of sulfur dye are short production process, low prices, good stability, convenient application and it is a popular dye which can be applied to the dyeing of fiber, such as cotton, linen, rayon, etc. However, sulfur dye is insoluble in water and when it is use do dye something it needs sodium sulfide or other reducing agents to reduce the dye into soluble leuco dye. Lecuo dye can be dyed on fibers because of its affinity to fibers, and then can be restored into its insoluble state after oxidation coloration so that it can fix on fiber. For ease of use, the common sulfur dyes are reacted with sodium sulfite or sodium hydrogen sulfite to produce thiosulfate of dye whose solubility is 150 g/l at 20° C. and can be used in continuous dyeing. However, it does not have affinity with the fibers and the dyeing liquor should be pad dyeing to the fiber and then treated with reducing solution to make the dye generate leuco dye with high affinity and can be attached to fibers. Then it should be watered and oxidation fixing the color. The feature of this dye is good levelness. However, it is not common to applied in the dyeing cellulose fibers, but often applied in paper dyeing. Introducing carboxyl group to sulfur dye structure to synthesize carboxylic acid type sulfur dye which can not only give good water solubility to the dye but also make the dye can be combined with fiber (cotton, wool, silk and leather) with the covalent bonds by making use of the reaction of carboxyl group and therefore gives sulfur dye good application features. As a result, the development of carboxylic acid type sulfur dye in recent years has caught people's attention.

U.S. Pat. No. 5,383,961 use common sulfur leuco dyes to react with chloroacetic acid in aqueous medium to prepare carboxylic acid type water-soluble sulfur dyes with good water solubility and the contents of carboxyl groups are between 5 to 20%. The salt-free dyes synthesized can be obtained with precipitating in acid, filtering, washing with water, and the salt can also be removed with membrane separation. Professor ZHANG Shufen from Dalian University of Technology uses Sulphur Black to react with chloroacetic acid to obtain carboxylic acid type water-soluble sulfur dyes and the carboxyl group content of dye reaches 11.9% (Chinese Chemical Letters, 2005, 16 (4): 554-556; Coloration Technology, 2007, 123 (3):191-196).

Water-soluble sulfur dye containing carboxyl group is a research direction of the improvement and gentrification of sulfur dye. Currently, the only reported carboxylic acid type sulfur dyes are generated by the reaction of sulfur dyes with α-chlorinated carboxylic acid. There is no research on carboxylic acid water-soluble sulfur dyes generated by the reaction of sulfur dyes with other active compounds containing carboxylic acid to introduce the carboxyl group into the dye.

SUMMARY OF THE INVENTION

An objective of the present invention is to provide a novel carboxylic acid type water-soluble sulfur dye. It is obtained by reacting leuco dye reduced from common sulfur dyes with active compounds containing carboxyl groups (such as compounds containing halogen, double bonds, s-triazine or chloroacetyl group). This dyes can be used to dye cotton, wool, silk and leather fiber. Because of its water-solubility and carboxyl group reactivity, the dyes have a simple product application process and good color fastness, thereby it has broad application prospects.

In order to achieve the above objectives, the present invention is embodied by the follow technical solution relating:

A carboxylic acid type water-soluble sulfur dye regards common sulfur dyes as parent A which has n water-soluble carboxyl groups of the general formula I:

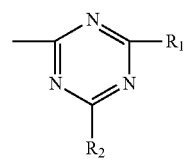

wherein:

$R_1$ and $R_2$ are each independently selected from the group consisting of Cl, F, OH, formula I a, formula I b and formula I c, and $R_1$ and $R_2$ can not simultaneously be Cl, F or OH;

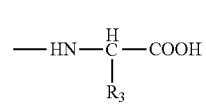

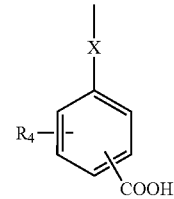

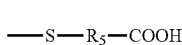

$R_3$ is selected form the group consisting of H, $CH_3$, $(CH_3)_2CH$, $CH_3CH(CH_3)CH_2$, $CH_3CH_2CH(CH_3)$, $CH_2OH$, $HSCH_2$, $CH_3SCH_2CH_2$, $C_5H_6CH_2$, $CH_2COOH$ and $CH_2CH_2COOH$;

$R_4$ is selected from the group consisting of H, Cl, Br, $CH_3$, OH, $NH_2$, $NO_2$ and COOH;

$R_5$ is selected from the group consisting of $-CH_2-$, $-CH_2CH_2-$, $-CH(CH_3)-$, $-CH(CH_2CH_3)-$ and $-CH(CH(SH)COOH)-$;

X is selected from the group consisting of NH and O;

n is an integer from 1 to 10.

In the preferred embodiment, the structure of the parent A in this invention further comprises at least a water soluble carboxyl group of the general formula II or the general formula III;

$$\begin{array}{c} R_6 \\ | \\ -C-COOH \\ | \\ Y \end{array} \quad \text{II}$$

$$-CH_2CO-R_{11} \quad \text{III}$$

The number of water soluble carboxyl groups of the general formula II is m;

The number of water soluble carboxyl groups of the general formula III is p;

wherein:

$R_6$ is selected from the group consisting of H, $CH_3CH=CH-$, COOH, $CH_2COOH$, $HOOCCH(OH)CH_2-$, $HOOCCH(Cl)CH_2-$, $HOOCCH(Cl)CH_2CH_2-$, $HOOCCH(Cl)CH_2CH_2CH_2-$ and $HOOCCH_2CH_2-$;

$R_{11}$ is selected from the group consisting of IIIa, IIIb and IIIc;

$$-HN-\underset{R_7}{\overset{H}{C}}-COOH \quad \text{IIIa}$$

$$\text{IIIb}$$
(benzene ring with Z, $R_8$, and COOH substituents)

$$-S-R_9-COOH \quad \text{IIIc}$$

$R_7$ is selected from the group consisting of H, $CH_3$, $(CH_3)_2CH$, $CH_3CH(CH_3)CH_2$, $CH_3CH_2CH(CH_3)$, $CH_2OH$, $HSCH_2$, $CH_3SCH_2CH_2$, $C_5H_6CH_2$, $CH_2COOH$ and $CH_2CH_2COOH$;

$R_8$ is selected from the group consisting of H, Cl, Br, $CH_3$, OH, $NH_2$, $NO_2$ and COOH;

$R_9$ is selected from the group consisting of $-CH_2-$, $-CH_2CH_2-$, $-CH(CH_3)-$, $-CH(CH_2CH_3)-$ and $-CH(CH(SH)COOH)-$;

Z is selected from the group consisting of NH and O;

Y is selected from the group consisting of H, $CH_3-$, $-COOH$ and $C_6H_5CH_2-$;

m is an integer from 0 to 10;

p is an integer from 0 to 10.

In this invention, the water soluble carboxyl group of general formula I is connected to the S atom of sulfhydryl group, the N atom of amino group or the O atom of hydroxyl group of parent A.

The water soluble carboxyl group of general formula II is connected to the S atom of sulfhydryl group, the N atom of amino group, or the O atom of hydroxyl group of parent A.

The water soluble carboxyl group of general formula III is connected to the S atom of sulfhydryl group, the N atom of amino group, or the O atom of hydroxyl group of parent A.

In this invention, the carboxylic acid type water-soluble sulfur dye contains 1 to 30% by weight of carboxyl groups.

In this invention, the common sulfur dye is a water-insoluble sulfur dye obtained with conventional ways, and the process of the preparation of the dye is known to one skilled in the art and unnecessary to go into details here.

In the preferred embodiment, the common sulfur dye is one of C.I. Sulphur Black 1, 2, 5, 6, 7, 10, 11, 12; or one of C.I. Sulphur Yellow 2, 9, 16, 19, 20; or one of C.I. Sulphur Orange 1, 3; or one of C.I. Sulphur Brown 8, 10, 12, 15, 16, 21, 51, 52, 63, 88, 90; or one of C.I. Sulphur Blue 2, 3, 5, 7, 9, 11, 13, 15, 19; or one of C.I. Sulphur Red 2, 6, 7, 10, 11, 12, 13, 14; or one of C.I. Sulphur Green 1, 2, 3, 6, 9, 19, 22, 25, 27, 31, 36, 37.

The structure of part of the active carboxylic compounds used for the synthesis of polycarboxylic acid sulfur dyes are as follows:

1#
$$HOOC-\underset{Cl}{CH}-COOH$$

2#
$$HOOC-\underset{Cl}{CH}-\underset{OH}{\overset{H}{C}}-COOH$$

3#
$$CH_3CH=\underset{Br}{C}-COOH$$

4#
$$HOOC-\underset{Cl}{CH}-\underset{Cl}{\overset{H}{C}}-COOH$$

5#
$$HOOC-\underset{Cl}{CH}-CH_2-\underset{Cl}{\overset{H}{C}}-COOH$$

6#
$$HOOC-\underset{Cl}{\overset{H}{C}}-CH_2-\overset{H_2}{C}-\underset{Cl}{\overset{H}{C}}-COOH$$

7#
$$HOOC-\underset{Cl}{\overset{H}{C}}-CH=CHCH_2-COOH$$

8#
$$\text{(triazine ring with Cl substituents)}-NH-\underset{CH_2-COOH}{\overset{H}{C}}-COOH$$

9#
$$\text{(triazine ring with Cl substituents)}-NH-\underset{CH_2CH_2-COOH}{\overset{H}{C}}-COOH$$

10#
$$\text{(triazine ring with Cl and two }NH-CH_2-COOH\text{ substituents)}$$

-continued
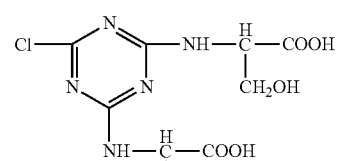
11#
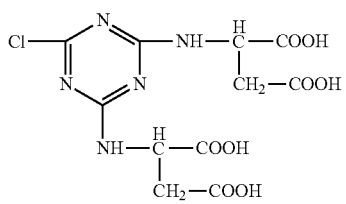
12#
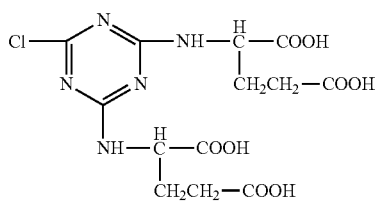
13#
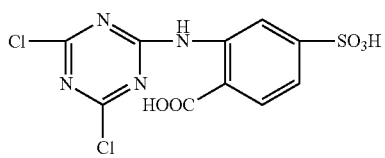
14#
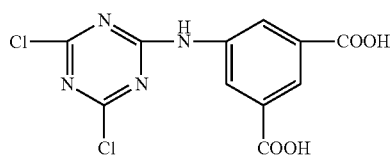
15#
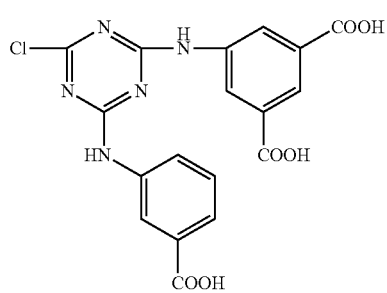
16#
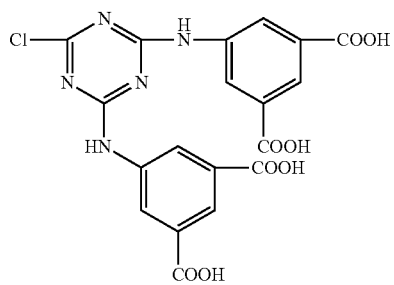
17#
-continued
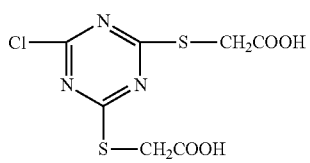
18#
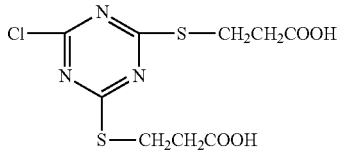
19#
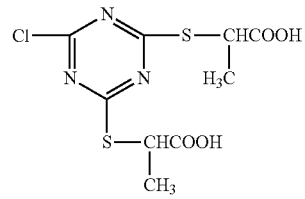
20#
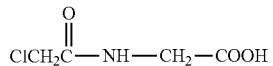
21#
22#
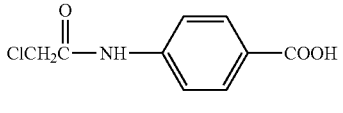
23#
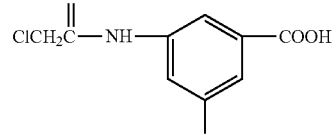
24#
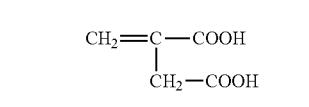
25#
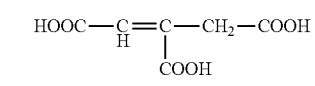
26#
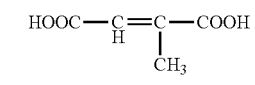
27#
28#
29#
30#

31#

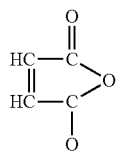

The present invention further provides a method for synthesizing the polycarboxylic acid type water-soluble sulfur dyes which includes the following steps: 1-10 g of sulfur dye, 1-5 g of sodium sulfide, 1-5 g of sodium hydroxide and 10-100 g of water are added into the high pressure vessel and heated to 80-180° C. and reacted for 2-20 hr. After the reaction, the mixture is cooled to room temperature. The high pressure vessel is opened and added 1-10 g of compound containing carboxyl group, 0.1-5 g of alkali and 10-100 g of water. The mixture is heated to 20-100° C. and reacted for 2-20 hr, cooled to room temperature. Open the high pressure vessel, 100-300 mL of 3% hydrochloric acid is added into the high pressure vessel in order to precipitate the dyes, and the precipitate is collected by filtration and drying to give the polycarboxylic acid type water-soluble sulfur dyes.

The carboxylic acid type water-soluble sulfur dyes provided by present invention makes use of carboxyl group to give the dye good solubility and high degree of dyeing, thus simplifying the application process of sulfur dye, expanding the range of applications and can be used for dyeing of leather, protein fibers. In addition, the introduction of carboxyl group gives the dye a reactive activity. The polycarboxylic acid type water-soluble sulfur dye make the dyeing fiber a good resistance to washing by forming an ester bond or an amide bond with fibers.

BRIEF DESCRIPTION OF THE DRAWINGS

FIG. 1 is the Infrared Spectrum of sulfur dyes having polycarboxylic group (product) and raw materials (reactant) in example 1.

DETAILED DESCRIPTION OF THE PREFERRED EMBODIMENTS

The following examples may enable ordinary technicians to fully understand this invention, but do not limit the invention in any manner.

Example 1

In a vessel with three openings equipped with a thermal couple, a reflux condenser and mechanical stirrer, 10 g of C.I. Sulphur Black 1, 5 g of sodium sulfide, 5 g of sodium hydroxide and 100 g of water are added into a high pressure vessel, the mixture is heated to 130° C. and reacted for 20 hr, and it turns into C.I. Sulphur Black 1 leuco dye. When the reaction is completed, cool the mixture to room temperature. Open the high pressure vessel and add 10 g of 8# compound containing carboxyl group, 5 g of sodium carbonate and 100 g of water into the vessel, and the mixture is heated to 50° C. and reacted for 10 hr, cooled to room temperature. Open the high pressure vessel, 300 mL of 3% hydrochloric acid is added into the vessel in order to precipitate the dyes, and the precipitate is collected by filtration, the filter cake is washed and dried to give the product.

Since the dye parent A does not contain carboxyl group, the carboxyl groups in the carboxylic acid type water-soluble sulfur dyes provided by this invention are all provided by substituent group of the general formula I, II, III; by measuring the content of carboxyl group in the carboxylic acid water-soluble sulfur dyes, it can reflect the content of carboxylic substituent group in the dyes provided by this invention.

The content of carboxyl group in product is measured by back titration, the results show that the dye contains about 26% by weight of carboxyl groups.

Examples 2-20

The method is the same as Example 1, but it uses respectively C.I. Sulphur Black 2, 5, 10; C.I. Sulphur Yellow 2, 20; C.I. Sulfur orange 1, 3; C.I. Sulphur Brown 8, 21, 90; C.I. Sulphur Blue 2, 9, 19; C.I. Sulphur Red 2, 12; C.I. Sulphur Green 1, 9, 25, 37 to replace C.I. Sulphur Black 1 to synthesize corresponding sulfur leuco dye and then reacts with 8# compound containing carboxyl group to obtain carboxylic acid type water-soluble sulfur dye. Other conditions are the same as in Example 1.

Examples 21-23

The method is the same as Example 1, namely, use 9#, 14#, 15# compound containing carboxyl group to replace 8# compound in Example 1 to react with C.I. Sulphur Black 1 leuco dye to obtain a carboxylic acid type water-soluble sulfur dye. Other conditions are the same as in Example 1.

Example 24

In a vessel with three openings equipped with a thermal couple, a reflux condenser and mechanical stirrer, 10 g of C.I. Sulphur Black 1, 5 g of sodium sulfide, 5 g of sodium hydroxide and 100 g of water are added into a high pressure reactor, the mixture is heated to 140° C. and reacted for 18 hr, and it turns into C.I. Sulphur Black 1 leuco dye. When the reaction is completed, cool the mixture to room temperature. Open the high pressure reactor and add 10 g of 10# compound containing carboxyl group, 5 g of sodium carbonate and 100 g of water into the reactor, and the mixture is heated to 90° C. and reacted for 6 hr, cooled to room temperature. Open the high pressure reactor, 300 mL of 3% hydrochloric acid is added into the reactor in order to precipitate the dyes, and the precipitate is collected by filtration, the filter cake is washed and dried to give the product. The content of carboxyl group in product is measured by back titration, the results show that the dye contains about 24% by weight of carboxyl groups.

Examples 25-43

The method is the same as Example 24, namely, use sulfur leuco dye synthesized in Examples 2-20 to replace C.I. Sulphur Black 1 leuco dye in Example 24 to react with 10# compound containing carboxyl group to obtain a carboxylic acid type water-soluble sulfur dye. Other conditions are the same as in Example 24.

Examples 44-50

The method is the same as Example 24, namely, use 11-13#, 16-20# compound containing carboxyl group to replace 10# compound in Example 24 to react with C.I. Sulphur Black 1 leuco dye to obtain a carboxylic acid type water-soluble sulfur dye. Other conditions are the same as in Example 24.

Example 51

In a vessel with three openings equipped with a thermal couple, a reflux condenser and mechanical stirrer, 10 g of C.I. Sulphur Black 1, 5 g of sodium sulfide, 5 g of sodium hydroxide and 100 g of water are added into the high pressure vessel, the mixture is heated to 150° C. and reacted for 20 hr, and it turns into C.I. Sulphur Black 1 leuco dye. When the reaction is completed, cool the mixture to room temperature. Open the high pressure vessel and add 5 g of 21# compound containing carboxyl group, 5 g of sodium carbonate and 100 g of water into the vessel, and the mixture is heated to 100° C. and reacted for 8 hr, cooled to room temperature. Open the high pressure vessel, 300 mL of 3% hydrochloric acid is added into the vessel in order to precipitate the dyes, and the precipitate is collected by filtration, the filter cake is washed and dried to give the product. The content of carboxyl group in product is measured by back titration, the results show that the dye contains about 12% by weight of carboxyl groups.

Examples 52-70

The method is the same as Example 51, namely, use sulfur leuco dye synthesized in Examples 2-20 to replace C.I. Sulphur Black 1 leuco dye in Example 51 to react with 21# compound containing carboxyl group to obtain a carboxylic acid type water-soluble sulfur dye. Other conditions are the same as in Example 51.

Example 71-75

The method is the same as Example 51, namely, use 22-26# compound containing carboxyl group to replace 21# compound in Example 51 to react with C.I. Sulphur Black 1 leuco dye to obtain a carboxylic acid type water-soluble sulfur dye. Other conditions are the same as in Example 51.

Example 76

In a vessel with three openings equipped with a thermal couple, a reflux condenser and mechanical stirrer, 10 g of C.I. Sulphur Black 1, 5 g of sodium sulfide, 5 g of sodium hydroxide and 100 g of water are added into the high pressure vessel, the mixture is heated to 130° C. and reacted for 10 hr, it turns into C.I. Sulphur Black 1 leuco dye. When the reaction is completed, cool the mixture to room temperature. Open the high pressure vessel and add 5 g of 1# compound containing carboxyl group, 5 g of sodium carbonate and 100 g of water into the vessel, and the mixture is heated to 70° C. and reacted for 8 hr, cooled to room temperature. Open the high pressure vessel, 300 mL of 3% hydrochloric acid is added into the vessel in order to precipitate the dyes, and the precipitate is collected by filtration, the filter cake is washed and dried to give the product. The content of carboxyl group in product is measured by back titration, the results show that the dye contains about 21% by weight of carboxyl groups.

Examples 77-95

The method is the same as Example 76, namely, use C.I. Sulphur Black 2, 5, 10; C.I. Sulphur Yellow 2, 20; C.I. Sulfur orange 1, 3; C.I. Sulphur Brown 8, 21, 90; C.I. Sulphur Blue 2, 9, 19; C.I. Sulphur Red 2, 12; C.I. Sulphur Green 1, 9, 25, 37 to replace C.I. Sulphur Black 1 which is added into the high pressure vessel with sodium sulfide, sodium hydroxide and water for the reaction. When the reaction is completed, cool the mixture to room temperature. Open the high pressure vessel and add 1# compound containing carboxyl group, sodium carbonate and 10~100 g of water. After the reaction, 3% hydrochloric acid is added into the high pressure vessel in order to precipitate the dyes, and the precipitate is collected by filtration, the filter cake is washed and dried to give the product. Other conditions are the same as in Example 76.

Examples 96-101

The method is the same as Example 1, namely, use 2-7# compound containing carboxyl group to replace 1# compound in Example 1 to react with C.I. Sulphur Black 1 leuco dye to obtain a carboxylic acid type water-soluble sulfur dye. Other conditions are the same as in Example 1.

Example 102

In a vessel with three openings equipped with a thermal couple, a reflux condenser and mechanical stirrer, 10 g of C.I. Sulphur Black 1, 5 g of sodium sulfide, 5 g of sodium hydroxide and 100 g of water are added into a high pressure vessel, the mixture is heated to 130° C. and reacted for 10 hr, it turns into C.I. Sulphur Black 1 leuco dye. When the reaction is completed, cool the mixture to room temperature. Open the high pressure vessel and add 10 g of 27# compound containing carboxyl group, 5 g of sodium carbonate and 100 g of water into the vessel, and the mixture is heated to 100° C. and reacted for 20 hr, cooled to room temperature. Open the high pressure vessel, 300 mL of 3% hydrochloric acid is added into the vessel in order to precipitate the dyes, and the precipitate is collected by filtration, the filter cake is washed and dried to give the product. The content of carboxyl group in product is measured by back titration, the results show that the dye contains about 23% by weight of carboxyl groups.

Examples 103-121

The method is the same as Example 102, namely, use sulfur dye leuco dye synthesized in Examples 2-20 to replace C.I. Sulphur Black 1 leuco dye in Example 102 to react with 27# compound containing carboxyl group to obtain a carboxylic acid type water-soluble sulfur dye. Other conditions are the same as in Example 102.

Examples Original of 122-125

The method is the same as Example 102, namely, use 28-31# compound containing carboxyl group to replace 27# compound in Example 102 to react with C.I. Sulphur Black 1 leuco dye to obtain a carboxylic acid type water-soluble sulfur dye. Other conditions are the same as in Example 102.

Example 126

In a vessel with three openings equipped with a thermal couple, a reflux condenser and mechanical stirrer, 10 g of C.I. Sulphur Black 1, 5 g of sodium sulfide, 5 g of sodium hydroxide and 100 g of water are added into a high pressure vessel, the mixture is heated to 140° C. and reacted for 20 hr, it turns into C.I. Sulphur Black 1 leuco dye. When the reaction is completed, cool the mixture to room temperature. Open the high pressure vessel and add 5 g of 1# compound containing carboxyl group, 5 g of 8# compound containing carboxyl group, 5 g of sodium carbonate and 100 g of water into the vessel, and the mixture is heated to 60° C. and reacted for 10 hr, cooled to room temperature. Open the high pressure vessel, 300 mL of 3% hydrochloric acid is added into the vessel in order to precipitate the dyes, and the precipitate is collected by filtration, the filter cake is washed and dried to give the product. The content of carboxyl group in product is measured by back titration, the results show that the dye contains about 29% by weight of carboxyl groups.

Examples 127-145

The method is the same as Example 126, namely, use sulfur dye leuco dye synthesized in Examples 2-20 to replace C.I. Sulphur Black 1 leuco dye in Example 126 to react with 1# and 8# compound containing carboxyl group to obtain a carboxylic acid water-soluble sulfur dye. Other conditions are the same as in Example 126.

Examples 146-151

The method is the same as Example 126, namely, use 2-7# compound containing carboxyl group to replace 1# compound in Example 126 to react with C.I. Sulphur Black 1 leuco dye and 8# compound containing carboxyl group to obtain a carboxylic acid water-soluble sulfur dye. Other conditions are the same as in Example 126.

Examples 152-163

The method is the same as Example 126, namely, use 9-20# compound containing carboxyl group to replace 8# compound in Example 126 to react with C.I. Sulphur Black 1 leuco dye and 1# compound containing carboxyl group to obtain a carboxylic acid water-soluble sulfur dye. Other conditions are the same as in Example 126.

Example 164

In a vessel with three openings equipped with a thermal couple, a reflux condenser and mechanical stirrer, 10 g of C.I. Sulphur Black 1, 5 g of sodium sulfide, 5 g of sodium hydroxide and 100 g of water are added into a high pressure vessel, the mixture is heated to 170° C. and reacted at for 6 hr, it turns into C.I. Sulphur Black 1 leuco dye. When the reaction is completed, cool the mixture to room temperature. Open the high pressure vessel and add 2 g of 1# compound containing carboxyl group, 2 g of 8# compound containing carboxyl group, 2 g of 21# compound containing carboxyl group, 5 g of sodium carbonate and 100 g of water into the vessel, and the mixture is heated to 80° C. and reacted for 20 hr, cooled to room temperature. Open the high pressure vessel. 300 mL of 3% hydrochloric acid is added into the vessel in order to precipitate the dyes, and the precipitate is collected by filtration, the filter cake is washed and dried to give the product. The content of carboxyl group in product is measured by back titration, the results show that the dye contains about 16% by weight of carboxyl groups.

Examples 165-183

The method is the same as Example 164, namely, use sulfur dye leuco dye synthesized in Examples 2-20 to replace C.I. Sulphur Black 1 leuco dye in Example 164 to react with 1#, 8# and 21# compounds containing carboxyl group to obtain a carboxylic acid type water-soluble sulfur dye. Other conditions are the same as in Example 164.

Examples 184-188

The method is the same as Example 164, namely, use 22-26# compound containing carboxyl group to replace 21# compound in Example 164 to react with C.I. Sulphur Black 1 leuco dye, 8# and 1# compounds containing carboxyl group to obtain a carboxylic acid type water-soluble sulfur dye. Other conditions are the same as in Example 164.

Examples 189-200

The method is the same as Example 164, namely, use 9-20# compound containing carboxyl group to replace 8# compound in Example 164 to react with C.I. Sulphur Black 1 leuco dye, 1# and 21# compounds containing carboxyl group to obtain a carboxylic acid water-soluble sulfur dye. Other conditions are the same as in Example 164.

Example 201

In a vessel with three openings equipped with a thermal couple, a reflux condenser and mechanical stirrer, 10 g of C.I. Sulphur Black 1, 5 g of sodium sulfide, 5 g of sodium hydroxide and 100 g of water are added into a high pressure vessel, the mixture is heated to 120° C. and reacted for 10 hr, it turns into C.I. Sulphur Black 1 leuco dye. When the reaction is completed, cool the mixture to room temperature. Open the high pressure vessel and add 1 g of 1# compound containing carboxyl group, 1 g of 21# compound containing carboxyl group, 5 g of sodium carbonate and 100 g of water into the vessel, and the mixture is heated to 80° C. and reacted for 8 hr, cooled to room temperature. Open the high pressure vessel, 300 mL of 3% hydrochloric acid is added into the vessel in order to precipitate the dyes, and the precipitate is collected by filtration, the filter cake is washed and dried to give the product. The content of carboxyl group in product is measured by back titration, the results show that the dye contains about 4% by weight of carboxyl groups.

Examples 202-220

The method is the same as Example 201, namely, use sulfur dye leuco dye synthesized in Examples 2-20 to replace C.I. Sulphur Black 1 leuco dye in Example 201 to react with 1# and 21# compounds containing carboxyl group to obtain a carboxylic acid type water-soluble sulfur dye. Other conditions are the same as in Example 201.

Examples 221-225

The method is the same as Example 201, namely, use 22-26# compound containing carboxyl group to replace 21# compound in Example 201 to react with C.I. Sulphur Black 1 leuco dye and 1# compounds containing carboxyl group to obtain a carboxylic acid water-soluble sulfur dye. Other conditions are the same as in Example 201.

Example 226

In a vessel with three openings equipped with a thermal couple, a reflux condenser and mechanical stirrer, 10 g of C.I. Sulphur Black 1, 5 g of sodium sulfide, 5 g of sodium hydroxide and 100 g of water are added into a high pressure vessel, the mixture is heated to 140° C. and reacted for 12 hr, it turns into C.I. Sulphur Black 1 leuco dye. When the reaction is completed, cool the mixture to room temperature. Open the high pressure vessel and add 2 g of 8# compound containing carboxyl group, 2 g of 21# compound containing carboxyl group, 5 g of sodium carbonate and 100 g of water into the vessel, and the mixture is heated to 90° C. and reacted for 10 hr, cooled to room temperature. Open the high pressure vessel, 100-300 mL of 3% hydrochloric acid is added into the vessel in order to precipitate the dyes, and the precipitate is collected by filtration, the filter cake is washed and dried to give the product. The content of carboxyl group in product is measured by back titration, the results show that the dye contains about 11% by weight of carboxyl groups.

Examples 227-238

The method is the same as Example 226, namely, use 9-20# compound containing carboxyl group to replace 8# compound in Example 226 to react with C.I. Sulphur Black 1 leuco dye and 21# compound containing carboxyl group to obtain a carboxylic acid type water-soluble sulfur dye. Other conditions are the same as in Example 226.

Example 239

In a vessel with three openings equipped with a thermal couple, a reflux condenser and mechanical stirrer, 10 g of C.I. Sulphur Black 1, 5 g of sodium sulfide, 5 g of sodium hydroxide and 100 g of water are added into a high pressure vessel, the mixture is heated to 130° C. and reacted for 4 hr, it turns into C.I. Sulphur Black 1 leuco dye. When the reaction is completed, cool the mixture to room temperature. Open the high pressure vessel and add 1 g of 1# compound containing carboxyl group, 1 g of 8# compound containing carboxyl group, 1 g of 21# compound containing carboxyl group, 5 g of sodium carbonate and 100 g of water into the vessel, and the mixture is heated to 80° C. and reacted for 8 hr, cooled to room temperature. Open the high pressure vessel. 300 ml of 3% hydrochloric acid is added into the vessel in order to precipitate the dyes, and the precipitate is collected by filtration, the filter cake is washed and dried to give the product. The content of carboxyl group in product is measured by back titration, the results show that the dye contains about 8% by weight of carboxyl groups.

Examples 240-244

The method is the same as Example 239, namely, use 22-26# compound containing carboxyl group to replace 21# compound containing carboxyl group in Example 239 to react with C.I. Sulphur Black 1 leuco dye, 1# and 8# compounds containing carboxyl group to obtain a carboxylic acid type water-soluble sulfur dye. Other conditions are the same as in Example 239.

Example 245

In a vessel with three openings equipped with a thermal couple, a reflux condenser and mechanical stirrer, 10 g of C.I. Sulphur Black 1, 5 g of sodium sulfide, 5 g of sodium hydroxide and 100 g of water are added into a high pressure vessel, the mixture is heated to 140° C. and reacted for 10 hr, it turns into C.I. Sulphur Black 1 leuco dye. When the reaction is completed, cool the mixture to room temperature. Open the high pressure vessel and add of 3 g 1# compound containing carboxyl group, 3 g of 27# compound containing carboxyl group, 5 g of sodium carbonate and 100 g of water into the vessel, and the mixture is heated to 100° C. and reacted for 4 hr, cooled to room temperature. Open the high pressure vessel, 300 mL of 3% hydrochloric acid is added into the vessel in order to precipitate the dyes, and the precipitate is collected by filtration, the filter cake is washed and dried to give the product. The content of carboxyl group in product is measured by back titration, the results show that the dye contains about 16% by weight of carboxyl groups.

Examples 246-264

The method is the same as Example 245, namely, use sulfur dye leuco dye synthesized in Examples 2-20 to replace C.I. Sulphur Black 1 leuco dye in Example 245 to react with 1# and 27# compounds containing carboxyl group to obtain a carboxylic acid type water-soluble sulfur dye. Other conditions are the same as in Example 245.

Example 265-269

The method is the same as Example 245, namely, use 28-31# compound containing carboxyl group to replace 27# compound in Example 245 to react with C.I. Sulphur Black 1 leuco dye and 1# compound containing carboxyl group to obtain a carboxylic acid type water-soluble sulfur dye. Other conditions are the same as in Example 245.

Example 270

In a vessel with three openings equipped with a thermal couple, a reflux condenser and mechanical stirrer, 10 g of C.I. Sulphur Black 1, 5 g of sodium sulfide, 5 g of sodium hydroxide and 100 g of water into a high pressure vessel, the mixture is heated to 170° C. and reacted for 20 hr, it turns into C.I. Sulphur Black 1 leuco dye. When the reaction is completed, cool the mixture to room temperature. Open the high pressure vessel and add 2 g of 1# compound containing carboxyl group, 2 g of 27# compound containing carboxyl group, 2 g of 10# compound containing carboxyl group, 5 g of sodium carbonate, 100 g of water into the vessel, and the mixture is heated to 80° C. and reacted for 16 hr, cooled to room temperature. Open the high pressure vessel, 300 mL of 3% hydrochloric acid is added into the vessel in order to precipitate the dyes, and the precipitate is collected by filtration, the filter cake is washed and dried to give the product. The content of carboxyl group in product is measured by back titration, the results show that the dye contains about 15% by weight of carboxyl groups.

Examples 271-289

The method is the same as Example 270, namely, use sulfur dye leuco dye synthesized in Examples 2-20 to replace C.I. Sulphur Black 1 leuco dye in Example 270 to react with 1#, 27# and 8# compounds containing carboxyl group to obtain a carboxylic acid type water-soluble sulfur dye. Other conditions are the same as in Example 270.

Examples 290-315

The method is the same as Example 270, namely, use 2-9, 11-26, 28-31# compound containing carboxyl group to replace 27# compound in Example 270 to react with C.I. Sulphur Black 1 leuco dye and 8# compound containing carboxyl group to obtain a carboxylic acid type water-soluble sulfur dye. Other conditions are the same as in Example 270.

Example 316

In a vessel with three openings equipped with a thermal couple, a reflux condenser and mechanical stirrer, 10 g of C.I. Sulphur Black 1, 5 g of sodium sulfide, 5 g of sodium hydroxide and 100 g of water are added into a high pressure vessel, the mixture is heated to 140° C. and reacted for 18 hr, it turns into C.I. Sulphur Black 1 leuco dye. When the reaction is completed, cool the mixture to room temperature. Open the high pressure vessel and add 2 g of 1# compound containing carboxyl group, 2 g of 8# compound containing carboxyl group, 2 g of 10# compound containing carboxyl group, 2 g of 21# compound containing carboxyl group, 2 g of 27# compound containing carboxyl group, 5 g of sodium carbonate and 100 g of water into the vessel, and the mixture is heated to 100° C. and reacted for 10 hr, cooled to room temperature. Open the high pressure vessel. 300 mL of 3% hydrochloric acid is added into the vessel in order to precipitate the dyes, and the precipitate is collected by filtration, the filter cake is washed and dried to give the product. The content of carboxyl group in product is measured by back titration, the results show that the dye contains about 27% by weight of carboxyl groups.

The followings are the application examples of carboxylic acid type water-soluble sulfur dye prepared by the examples of this invention.

Example 317

5-10 g of carboxylic acid type sulfur dye synthesized in Example 1, 0.5-1 g of sodium carbonate and water are mixed into dye liquor with a concentration of 8%. Pad dyeing of cotton fiber is carried out using the dye liquor containing 7% imidazole, 5% ammonium nitrate and 2% urea at a condition of liquor ratio of 1:10, liquid pick-up of 70-80%. The dyeing procedure, comprising the following steps in sequence: double-dip-double-nip, pre-baking at 80° C. for 5 min, baking at 190° C. for 3 min, washing with water, soaping with 2% of OP-10 at 95° C. for 15 min, and washing and drying. The dye uptake is above 95% determined from the calibration curve.

Examples 318-323

The method is the same as Example 317, namely, use the carboxylic acid type sulfur dye synthesized in Example 24, 51, 76, 102, 126, 270 to replace carboxylic acid type sulfur dye synthesized in Example 1 to dye the cotton fiber, and measurement of the dye uptake of cotton fibers are all more than 95%.

Example 324

5-10 g of carboxylic acid type sulfur dye synthesized in Example 126, 0.5-1 g of sodium carbonate are mixed into dye liquor with a concentration of 0.5-5% and then transfer dye liquor to the dyeing drum, add the leather into the drum. The mixture is heated to 40-80° C. and kept at this temperature for 1 hour, Sima's Fatliquor BA is then added into the dyeing drum and turn on the drum for 60 min, formic acid is added to adjust pH to around 3.5, turn the drum on for 30 min. The leather is washed with water. Combine the residue liquor and washing liquid, fix the volume and measure its absorbance. The dye uptake is above 96% determined from the calibration curve.

Examples 325-330

The method is the same as Example 324, namely, use the carboxylic acid type sulfur dye synthesized in Example 1, 33, 61, 115, 143, 166 to replace carboxylic acid type sulfur dye synthesized in Example 1 to dye the cotton fiber and measurement of the dye uptake of cotton fibers are all more than 96%.

The invention claimed is:

1. A carboxylic acid type water-soluble sulfur dye comprising a parent compound and a number of carboxyl groups of formula I attached to the parent compound,

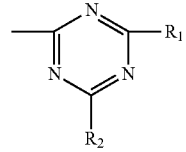

I wherein $R_1$ and $R_2$ are each independently selected from the group consisting of Cl, F, OH, formula Ia, formula Ib, and formula Ic, with the proviso that $R_1$ and $R_2$ are not simultaneously Cl, F, or OH;

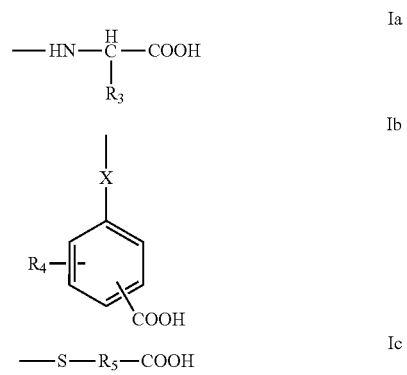

$R_3$ is selected form the group consisting of H, $CH_3$, $(CH_3)_2CH$, $CH_3CH(CH_3)CH_2$, $CH_3CH_2CH(CH_3)$, $CH_2OH$, $HSCH_2$, $CH_3SCH_2CH_2$, $C_5H_6CH_2$, $CH_2COOH$, and $CH_2CH_2COOH$; $R_4$ is selected from the group consisting of H, Cl, Br, $CH_3$, OH, $NH_2$, $NO_2$, and COOH;

$R_5$ is selected from the group consisting of $-CH_2-$, $-CH_2CH_2-$, $-CH(CH_3)-$, $-CH(CH_2CH_3)-$, and $-CH(CH(SH)COOH)-$; and X is selected from the group consisting of NH and O, wherein the parent compound is one selected from the group consisting of C.I. Sulphur Black 1, 2, 5, 6, 7, 10, 11, and 12; or one selected from the group consisting of C.I. Sulphur Yellow 2, 9, 16, 19, and 20; or one selected from the group consisting of C.I. Sulphur Orange 1 and 3; or one selected from the group consisting of C.I. Sulphur Brown 8, 10, 12, 15, 16, 21, 51, 52, 63, 88, and 90; or one selected from the group consisting of C.I. Sulphur Blue 2, 3, 5, 7, 9, 11, 13, 15, and 19; or one selected from the group consisting of C.I. Sulphur Red 2, 6, 7, 10, 11, 12, 13, and 14; or one selected from the group consisting of C.I. Sulphur Green 1, 2, 3, 6, 9, 19, 22, 25, 27, 31, 36, and 37.

2. The carboxylic acid type water-soluble sulfur dye according to claim 1, further comprising at least a carboxyl group chosen from formula II or formula III attached to the parent compound,

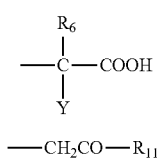 II

—CH₂CO—R₁₁   III wherein a number of water soluble carboxyl groups of the formula II is m, and a number of water soluble carboxyl groups of the formula III is p;

wherein $R_6$ is selected from the group consisting of H, $CH_3CH=CH-$, COOH, $CH_2COOH$, $HOOCCH(OH)CH_2-$, $HOOCCH(Cl)CH_2-$, $HOOCCH(Cl)CH_2CH_2-$, $HOOCCH(Cl)CH_2CH_2CH_2-$, and $HOOCCH_2CH_2-$;

$R_{11}$ is selected from the group consisting of IIIa, IIIb, and IIIc;

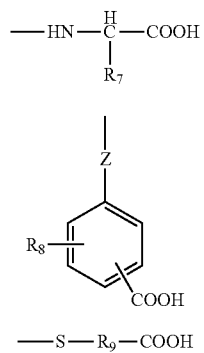

$R_7$ is selected from the group consisting of H, $CH_3$, $(CH_3)_2CH$, $CH_3CH(CH_3)CH_2$, $CH_3CH_2CH(CH_3)$, $CH_2OH$, $HSCH_2$, $CH_3SCH_2CH_2$, $C_5H_6CH_2$, $CH_2COOH$, and $CH_2CH_2COOH$;

$R_8$ is selected from the group consisting of H, Cl, Br, $CH_3$, OH, $NH_2$, $NO_2$, and COOH;

$R_9$ is selected from the group consisting of $-CH_2-$, $-CH_2CH_2-$, $-CH(CH_3)-$, $-CH(CH_2CH_3)-$, and $-CH(CH(SH)COOH)-$;

Z is selected from the group consisting of NH and O; and

Y is selected from the group consisting of H, $CH_3-$, —COOH and $C_6H_5CH_2$.

3. The carboxylic acid type water-soluble sulfur dye according to claim 2, wherein the parent compound comprises a sulfhydryl group, an amino group, or a hydroxyl group, where the carboxyl group of formula I, II or III is connected to the S atom of the sulfhydryl group, the N atom of the amino group, or the O atom of the hydroxyl group of parent A.

4. The carboxylic acid type water-soluble sulfur dye according to claim 1, wherein the carboxylic acid type water-soluble sulfur dye contains 1 to 30% by weight of carboxyl groups of formula I, wherein the weight of carboxyl groups is measured by back titration.

5. The carboxylic acid type water-soluble sulfur dye according to claim 1, wherein the number of carboxyl groups is an integer from 1 to 10.

6. The carboxylic acid type water-soluble sulfur dye according to claim 2, wherein m is an integer from 0 to 10 and p is an integer from 0 to 10, wherein m and p are not simultaneously zero.

\* \* \* \* \*